United States Patent [19]

Goldberg

[11] 4,157,717

[45] Jun. 12, 1979

[54] HYDRODYNAMIC EVACUATOR

[75] Inventor: Viktor Goldberg, Stuttgart, Fed. Rep. of Germany

[73] Assignee: Neumo Armaturenfabrik-Apparatebau-Metalligiesserei GmbH, Knittlingen, Fed. Rep. of Germany

[21] Appl. No.: 790,059

[22] Filed: Apr. 22, 1977

[30] Foreign Application Priority Data

Nov. 16, 1976 [DE] Fed. Rep. of Germany ....... 2652155

[51] Int. Cl.² ............................................. A61M 3/00
[52] U.S. Cl. .................................... 128/227; 128/276
[58] Field of Search ............... 128/227, 231, 276, 230, 128/275, 224

[56] References Cited

U.S. PATENT DOCUMENTS

| | | | |
|---|---|---|---|
| 1,479,451 | 1/1924 | Buckstein | 128/227 |
| 1,579,537 | 4/1926 | Hughens | 128/227 |
| 1,843,169 | 2/1932 | McKesson | 128/276 |
| 2,022,742 | 12/1935 | Salerni | 128/227 |
| 2,148,541 | 2/1939 | Dierker | 128/227 |
| 2,180,042 | 11/1939 | Ettinger | 128/276 |
| 2,646,042 | 7/1953 | Hsihu | 128/276 X |
| 3,410,268 | 11/1968 | Leucci | 128/227 |
| 3,780,736 | 12/1973 | Chen | 128/231 |

*Primary Examiner*—John D. Yasko
*Attorney, Agent, or Firm*—Charles E. Brown

[57] ABSTRACT

The disclosure describes a device for filling and evacuating hollow organs in human and animal bodies. The device is provided with a suction valve adapted to be connected to a catheter or probe, the suction valve being connected, by means of hoselines, to a storage tank for flushing liquids and to at least one collector vessel. The suction valve is in the form of a three-way element, one connection thereof being adapted to be connected directly to a catheter or probe, the inlet and outlet hoselines for the flushing liquid, connected to the said three-way valve, being of sufficient length to permit unobstructed actuation of the said catheter or probe, and of the said three-way valve independently of the storage tank and the collector vessel.

3 Claims, 3 Drawing Figures

HYDRODYNAMIC EVACUATOR

BACKGROUND OF THE INVENTION

1. Field of Invention

The invention relates to a device for filing and evacuating hollow organs in human and animal bodies, the said device being equipped with a suction valve adapted to be connected to a catheter or probe, the said suction valve being connected, by means of hoselines, with a storage tank for flushing liquids, and to at least one collector vessel.

2. Description of Prior Art

Various devices for flushing hollow organs in the human body, such as the stomach, intestines and bladder, are known in medicine. The bladder poses many problems, since fragments of calculus arising from lithotripsy, traces of tumour from the prostate or bladder after transurethral electrosection, and blood coagula from bladder tamponnade, must be removed therefrom.

Normal evacuation requires that the muscles in the wall of the hollow organ be capable of contracting, so that the organ is evacuated and no residue is left. This condition is met only in the case of a normal bladder, but not in the case of the stomach or intestine, or if the bladder is pathologically altered. Flushing is also inadequate for removing fragments of calculus arising from lithotripsy, traces of tissue after transurethral electrosection, and blood coagula from bladder tamponnade. Aspiration alone is unsuitable for removing such foreign bodies from the bladder.

There is no piece of equipment in clinical or practical use which meets these special clinical requirements. Furthermore, there is no known piece of equipment which can serve as an all-purpose unit. Aspiration units, such as water-jet pumps, vacuum bottles, and the like lead to a single evacuation of the hollow organ and to aspiration of the mucous membrane, and are therefore unsuitable for eliminating foreign bodies. Flushing of the stomach and the intestine by suction has the disadvantage that there is a considerable amount of dead space consisting of the volume of the hose inside and outside the body. When the funnel is filled, the air in this dead space is forced into the hollow organ and, when the said organ is evacuated, there is therefore some doubt as to whether what emerges is air or intestinal gas. Furthermore, the air and gases break up the column of liquid and halt the siphoning action. Even if the hose remains filled with liquid, the long hose causes oscillating flushing which is detrimental. Funnel-flushing also takes longer, adding to the patient's discomfort.

The so-called "balloon-evacuator" has been in use for about 100 years for eliminating fragments of calculus from the bladder after lithotripsy. The disadvantage of this is that the flushing fluid oscillates back and forth between the balloon and the bladder without being renewed. Thus any fragments of calculus, bacteria and blood are returned to the bladder each time the balloon is compressed, which is undesirable from the point of view of bladder cleaning and asepsis.

It has already been proposed to fill and evacuate the bladder in a continuous manner by means of an irrigator and a two-way instrument, with a collector vessel for fragments of calculus inserted into the outlet hose. Dividing the passage in the instrument into two, and inserting a viewing glass, restricts the inside diameter of the outlet duct, reduces very considerably the flow of flushing liquid and the ability to pass fragments of calculus and the like, and thus decreases the efficiency of the procedure.

SUMMARY OF INVENTION

It is therefore the purpose of the invention to provide a multi-purpose unit for filling hollow organs and evacuating them by suction. This unit is to provide reliable and sensitive operation, but without requiring additional operating personnel. Moreover the dead volume during flushing is to be reduced to a minimum.

According to the invention, this purpose is achieved by providing the suction valve in the form of a three-way element, one connection thereof being adapted to be directly connected to a catheter or probe, the inlet and outlet hose-lines for the flushing liquid, connected to the said three-way valve, being of sufficient length to permit unobstructed actuation of the said catheter or probe, and of the said three-way valve, independently of the storage tank and the collector vessel.

The hoselines running between the liquid-storage tank and the collector vessel, on the one hand, and the catheter or probe on the other hand, are long enough, preferably between 1 and 2 meters, to allow the three-way valve, the catheter, or the probe to be manipulated, without any need to move, or in any way alter, the liquid-storage tank or the collector vessel. It is of great advantage to locate the three-way valve in the immediate vicinity of the catheter or probe, since this reduces the so-called dead volume to a minimum, i.e. substantially to the volume of the catheter or probe. The whole unit may thus be operated in the immediate vicinity of the said catheter or probe.

The catheter is preferably in the form of an evacuating catheter and the probe in the form of a gastric or intestinal probe. These have only one passage through which the flushing liquid enters and leaves the hollow body.

The storage tank for the flushing liquid, and the collector vessel, are preferably arranged upon a common stand, where they remain even while the unit is in medical use.

According to the invention, therefore, the various receptacles and other parts of the device should be arranged as a single unit upon a stand, where they should also remain while the device is in use. It should preferably be possible to adjust the height of the storage tank on the stand. This makes it possible to adapt the pressure differential between the level of the liquid in the storage tank and the hollow organ to whatever procedure is to be carried out. It is also desirable to provide a means whereby this difference in height, or the distance above a specific zero, can be read off at any time. The said storage tank, and the lines running therefrom, are preferably mounted rotatably upon the stand, so that the directions in which the said lines run may be altered without moving the stand itself. The collector vessels may also be mounted rotatably upon the stand, although this is not essential. If a receptacle for calculus fragments is provided, this may be located immediately below the three-way valve. However, this receptacle may also be mounted, rotatably if necessary, upon the said stand, with connecting hoses of appropriate length between the said three-way valve and receptacle. It is preferable to provide an open receiver at the end of one outlet line, the capacity of which may be 10 liters, like that of the storage tank. According to one preferred embodiment of the invention, one outlet hose is terminated by an S-shaped piece of tube which is bent upwards and downwards, thus constituting a siphon. This prevents any air from rising back through the outlet line and thus interrupting a uniform suction, which is based upon hydrodynamic forces.

According to one particular embodiment of the invention, a special receptacle is provided for collecting large objects such as blood clots and small pieces of tissue, the said receptacle having an overflow and a continuous screen, the mesh size of which is larger than that of the screen which is used in a receptacle for collecting calculi or fragments thereof. A receptacle of this kind, for blood clots and small pieces of tissue may be in the form of a cylindrical beaker extended in an upward direction by means of a suitable screen, with an inlet tube extending almost to the bottom of the beaker. A receptacle of this kind retains blood clots and traces of tissue. Excess liquid can drain away, through the screen portion, into a receiver. Before the receptacle is opened, any liquid may also be poured out of the beaker through the screen, thus making it possible to obtain the blood clots and pieces of tissue separately from the liquid.

The three-way valve should be designed so that it can be operated with one hand. To this end the housing of the valve contains a cone acting as a valve plug, and mounted in the said housing so that it can be rotated 180° by means of a knurled operating wheel. This wheel is preferably located at the small end of the cone, the said housing having an oil chamber at the large end thereof. Applying pressure to the small end of the cone, against the force of a spring, makes it possible to loosen temporarily the seating of the cone in the housing, so that oil from the oil chamber may reach the sliding surface. This automatic lubrication may be carried out during flushing or evacuation, without interrupting the flushing procedure or dismantling the valve. This greatly increases the reliability of the device. The oil chamber is preferably filled with sterile oil, in order to prevent the sterility of the device from being impaired by this lubrication. The valve is preferably designed so that it may be dismantled and reassembled manually without any tools or other auxiliaries. Since all medical equipment must be completely dismantled each time it is sterilized, this design is very advantageous.

When the device is intended to be used, the storage tank is filled with warm sterile water after all of the parts thereof have been cleaned and sterilized. The three-way valve, and any shut-off valve fitted to the storage tank, is opened to provide a passage from the storage tank to the receiver, the hoselines being filled with water, or with the solution used, and all air being expelled. By setting the valve to provide a connection between the storage tank and the hollow organ in which the catheter or probe is located, the hollow organ may be filled and, by providing a connection between the hollow organ and the collector vessel, the hollow organ may be evacuated, the difference between the height of the column of liquid in the inlet system between the storage tank and the patient and, in the out-let system, between the patient and the collector vessel, providing the necessary pressure or suction. This may be achieved at will by adjusting the height of the storage tank and, possibly, of the collector vessel. This arrangement eliminates the possibility of an excessive positive pressure, such as may occur inadvertently with a balloon, and of an excessive negative pressure, such as may occur with a vacuum bottle.

In contrast to flushing by suction of the stomach and intestines, when gases appear in the outlet lines, it is possible, with the device according to the invention, to determine whether they are intestinal gases. If the column of liquid which produces the suction is interrupted by such gases, the said column may easily be restored with flushing liquid from the storage tank. In the flushing procedure, fresh flushing liquid reaches the hollow organ at each filling operation. Prior to the next flushing operation, the volume of liquid used for flushing may be drawn off substantially completely with little dead volume. Calculi, blood clots, and small pieces of tissue can be collected in receptacles connected as required.

The entire device may be operated by one person. It is desirable to equip the stand with a holder for the three-way valve, so that when the said valve is no longer needed, it can be unhooked to the stand, allowing the unit to be taken away as a whole without any dismantling.

BRIEF DESCRIPTION OF THE DRAWINGS

Additional characteristics of the invention may be gathered from the following description or embodiments thereof, as defined in the claims and described in the drawings attached hereto, wherein:

DESCRIPTION OF PREFERRED EMBODIMENT

Figure 1:
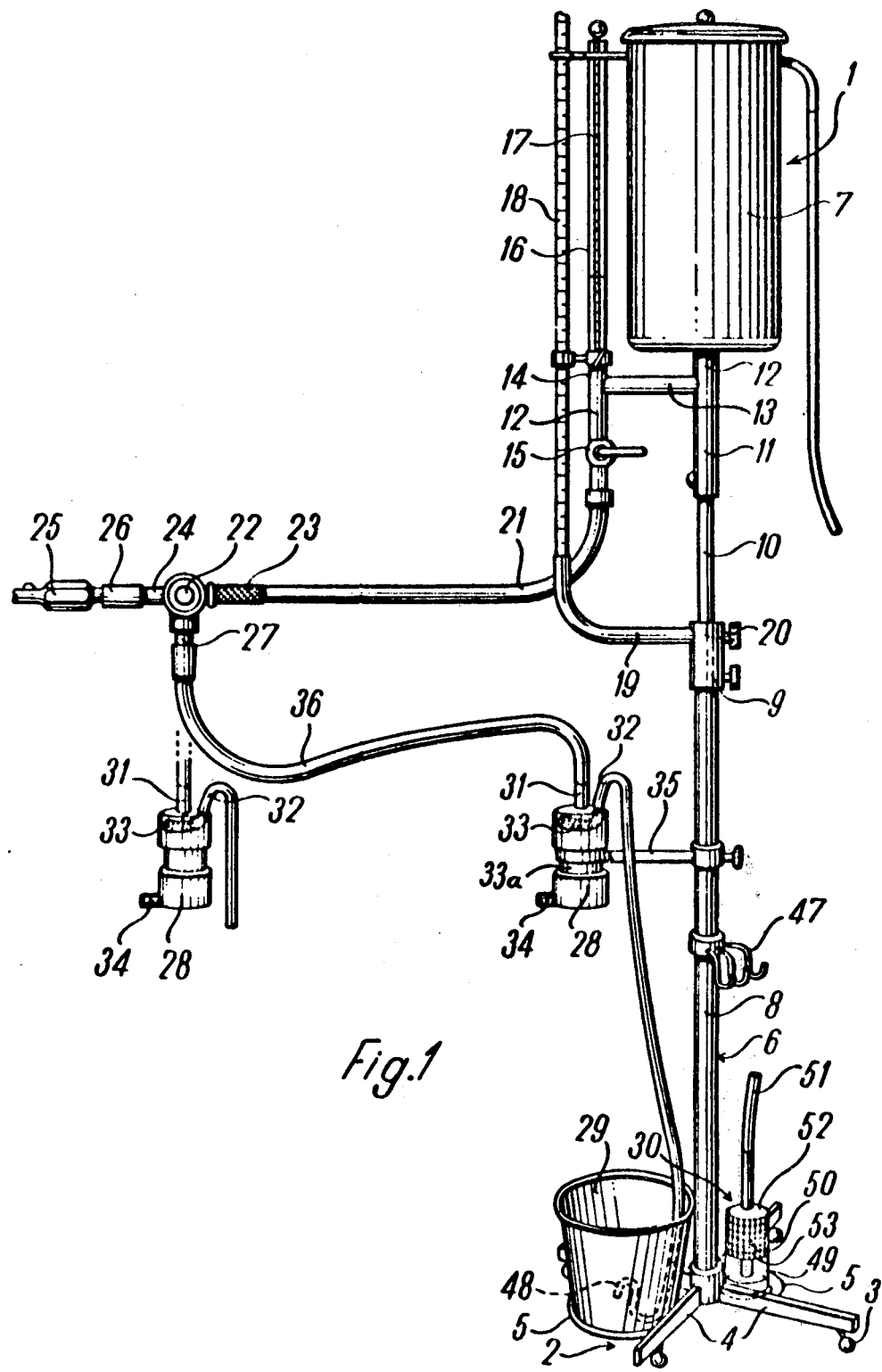
FIG. 1 is a full view of one embodiment according to the invention.
Figure 2:
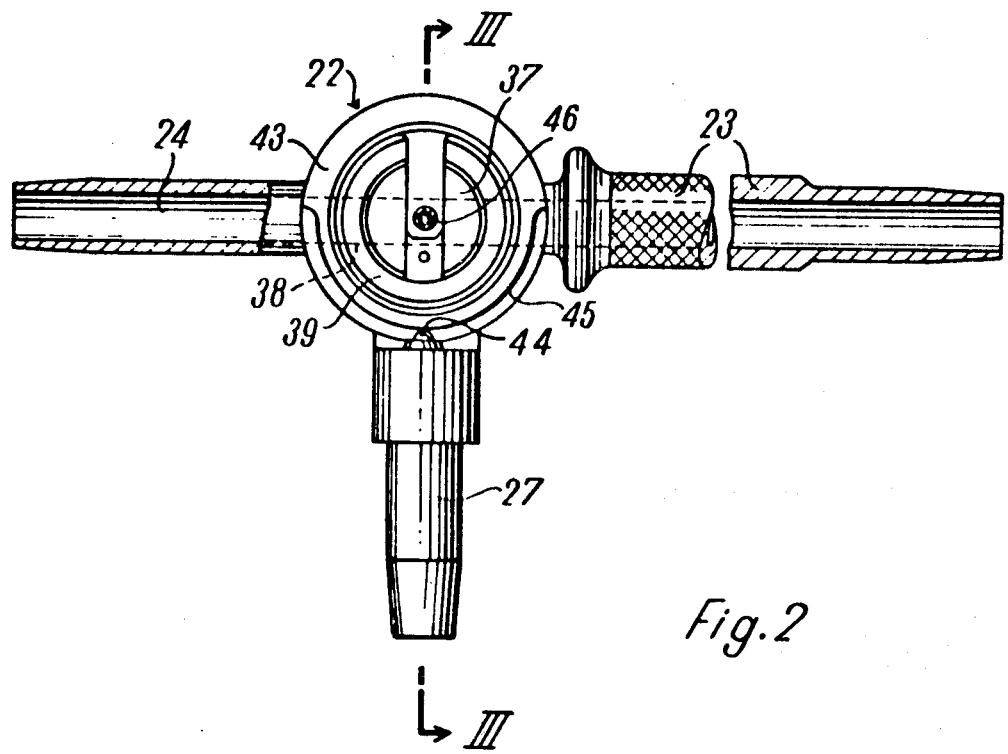
FIG. 2 shows the suction valve in partial section.
Figure 3:
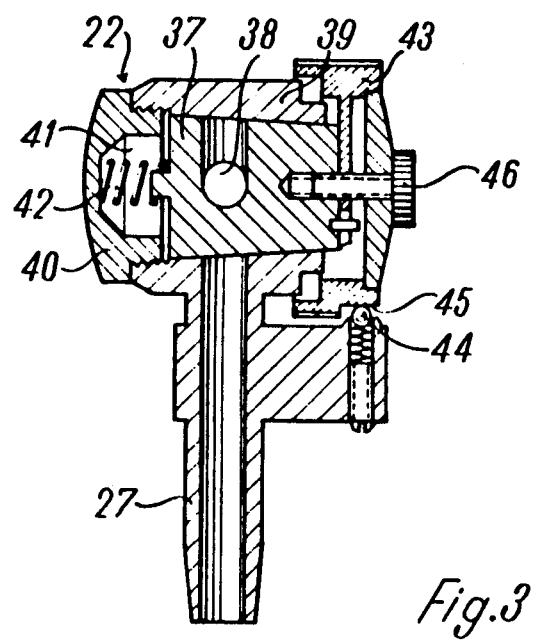
FIG. 3 is a section along line III—III of FIG. 2.

The drawing illustrates a device 1 for flushing an evacuating hollow organ of the human body, the device being in the form of a unit mounted on a stand 2 and movable therewith. Stand 2 has a four-legged base 4 equipped with casters 3, and supports 5 for buckets or the like, used as receivers, which supports are arranged between each pair of legs. Column 6 of the stand is adjustable in height and carries at its upper end a storage tank 7 for the flushing liquid. Lower tubular member 8 of this column, secured to base 4 terminates approximately at the height of a bed, where it is fitted with a locking screw 9 for an extension bar 10 inserted into tube 8. Storage tank 7 is of cylindrical design, it is provided with a cover, and has a capacity of 10 liters. Near the upper edge of storage tank 7 there is an inlet tube fitted with a hoseline through which the tank may be filled even when the cover is closed.

The underside of storage tank 7 is fitted with an axial tube running downwardly in the form of a sleeve 11 and fitting over the upper end of extension bar 10 of stand 2. The upper part of sleeve 11 is part of a drain tube 12 having a horizontal section 13. The latter opens into a section 14 running parallel with column 6 of the stand and with storage tank 7, the said section extending upwardly, as a measuring tube 16, as far as the upper edge of storage tank 7. The lower end of section 14 is fitted with a shut-off valve 15. The section of measuring tube adjacent the said storage tank is transparent and serves as a level indicator therefor. A thermometer 17 is inserted into measuring tube 16, the said thermometer extending downwardly at least as far as horizontal section 13 of drain pipe 12, so that the temperature of the flushing liquid flowing from storage tank 7 may be read off through the transparent section 16.

A measuring rod 18, carried by tubular part 8 of stand column 6, runs parallel with measuring tube 16 and carries a scale running in an upward direction. The said measuring rod has a lower horizontal support arm secured to an annular sleeve 20 surrounding extension bar 10 fitted to tube 8 of stand column 6, and comprising a locking screw, thus making the said measuring rod adjustable in height. Sleeves 20 and 11 are seated rotatably upon rod 10 and are connected together, so that measuring tube 16 and measuring rod 18 can both be rotated about stand 2, together with the storage tank.

A hose 21 runs from drain pipe 12 of storage tank 7 to a three-way suction valve 22. On the side to which hose 21 is connected, i.e. where the flushing liquid enters, the said valve is fitted with a piece of tube 23 acting as a grip. On the other side it has a nipple 24 for attaching an evacuating catheter, or a gastric or intestinal probe, by means of a short piece of hose 26. The liquid is drained through a nipple 27 fitted to the bottom portion of the said valve, from where a hose runs to a receptacle 28 for fragments of calculus and thence to a bucket 29 for the flushing liquid. The hose may also run directly to a receptacle 30, placed in a bucket, which collects small pieces of tissue and blood clots. Buckets 29 are located on stand supports 5 and may thus be moved with the said stand.

Calculus receptacle 28 is a transparent, waist high vessel having an inlet connector 31 and an adjacent outlet connector 32 just below its upper edge. Connector 32 is in the form of a piece of tube which passes through the wall of receptacle 28. Inside the receptacle, the piece of tube is perforated with a series of small holes and thus constitutes a screen 33. The overall cross-section of these small holes is larger than the flow cross-section of tube 32. In other words, the inside diameter of the system is 9 mm, while that of the hoselines, including the passages through valve 22 is about 10 mm.

Receptacle 28 has a closable aperture 34 through which fragments of calculus may be removed. The receptacle may be arranged substantially directly under three-way valve 22, with which it may move. On the other hand, it is also possible, as shown in FIG. 1, to secure the receptacle to stand 2 by means of a clamp 35, and to connect it to the said valve by means of a suitable length of hose, thus facilitating unobstructed manipulation of valve 22 and catheter 25 or the probe. Three-way valve 22, however, should always be as close as possible to the catheter or probe, in order to facilitate simultaneous manipulation, and to keep the dead volume between the end of the catheter and the valve as small as possible. To this end, only a short length of hose 26 is provided to connect the catheter to the valve. The stand column also carries a forked holder to which the suction valve may be hooked when device 1 is not in use.

Three-way valve 22 itself has a conical valve-plug 37 with passages 38 arranged in the form of a T in relation to each other and lying in a plane at right angles to the axis of the cone, the inside diameter of the said passages being 9 mm. The valve-plug or cone 37 is mounted to rotate 180° in a corresponding conical housing 39 of the said valve, a 90° turn from one terminal position leading to another passage in the cone. Valve 22 is closed off at the larger end of the cone by means of a screwed cover 40 forming an oil chamber 41. A coil spring 42 located between screwed cover 40 and cone 37 ensures satisfactory seating of the cone in housing 39. Fitted to the other end of the cone is a knurled operating wheel 43 which can be fitted to cone 37 only in a specific position defining the setting of the valve. Located in valve housing 39 is a spring-loaded ball 44, which bears against the edge of wheel 43 and snaps into a recess 45 therein when the said wheel reaches one of the straight-through settings of cone 37.

If axial pressure is applied to the smaller end of cone 37, or to a screw 46 which covers this end of the cone and secures knurled wheel 43 thereto, the said cone may easily be shifted axially, by about 0.5 to 1 mm, towards cover 40, thus allowing oil from oil chamber 1 to reach the sliding surfaces between the cone and valve housing 39, and lubricating and sealing the said valve. The latter is designed in such a manner that it may be dismantled and reassembled without any tools, which is highly important in sterilizing the unit.

Calculi, or fragments thereof, are collected in receptacle 28. To this end, screen tube 33 is designed in such a manner that solids larger than the size to be collected can no longer pass through the holes in the tube, but settle at the bottom of the receptacle. The waist 33a formed in this receptacle reduces the amount of flushing in the lower part thereof, and the fragments which settle upon the bottom are therefore not stirred up again.

The lower end of the hose running downwardly from receptacle 28 to bucket 29 is fitted with an S-shaped piece of tube bent up and then down. On the other hand, this acts as a siphon to prevent any upward return of air which would break down the suction column of liquid. On the other hand, it has the advantage, over a simple U-tube, of preventing the liquid from squirting up out of bucket 29.

Floor receptacle 30 is connected to the outlet end of three-way valve 22, instead of calculus receptacle 28, when small pieces of tissue or blood clots are being drawn out of the respective hollow organ. This receptacle consists of a lower, transparent, laterally-enclosed beaker part 49 from which a cylindrical grid part 50 extends upwardly. Inlet tube 51 passes through detachable cover 52 of the said receptacle and extends to about 3 cm above the bottom of beaker part 49. As soon as the level of the liquid in the receptacle reaches a height of 3 cm, air can no longer return upwardly. Openings 53 in grid part 50 are square and measure about 4 mm. Thus blood clots and small pieces of tissue are retained in the receptacle, whereas the liquid, e.g. the flushing liquid, can drain through the grid into bucket 29 in which receptacle 30 is located.

If device 1 is to be used merely to evacuate a hollow organ, the three-way valve is set to establish a free passage from storage tank 7 downwardly to bucket 29 (position I). After shut-off valve 15 is opened, water flows from the storage tank and fills up the hoselines. The three-way valve is then set to establish a passage between catheter 25 and bucket 29 (position III), so that the column of liquid in the hoselines under the three-way valve can produce suction and evacuate the hollow organ through the catheter. If the hollow organ is to be filled, the three-way valve is set to provide a passage from storage tank 7 to the said hollow organ (position II), and the organ is thus filled with flushing liquid. The liquid may then be removed from the organ again as before (position III), by setting the three-way valve to provide a passage between the hollow organ and the receiving bucket. Since the distance between the free end of the catheter and the three-way valve is very short, the dead volume moved back and forth during the flushing operation is quite small, and an intensive exchange of the liquid in the hollow organ is achieved. If the column of liquid producing the suction is broken down, for example because the hollow organ contains gases and these are also being evacuated, the column of liquid may easily be built up again by setting the three-way valve back again to provide a free passage from storage tank 7 to bucket 29 (position I).

Since the stand is adjustable in height, the hydrostatic pressure of the flushing liquid in the hollow organ may be varied. The actual pressure may be determined at any time by reading off the level of the liquid in measuring tube 16 with the aid of measuring rod 18 arranged immediately adjacent the said measuring tube. Measuring rod 18 and measuring tube 16 are connected together to permit parallel displacement. The height of the said measuring rod therefore remains unchanged when storage tank 7 is raised or lowered by means of extension bar 10. As mentioned previously the zero point on the said measuring rod is adjusted approximately to the level of the patient. It the patient is not on the same level as the said zero point, this is corrected by adjusting the height of arm 19 by means of clamping ring 20.

Since the stand is mobile, and since drain tube 12, measuring tube 16, and measuring rod 18 can be rotated about the said stand, the catheter, the probe, and the three-way valve may also be manipulated in practice without obstruction and without being affected by the lines and equipment connected thereto. Except for the transparent parts and the hoses, substantially all parts of device 1 are made of high-grade steel or chromium-plated brass, thus providing a rugged and easily cleaned unit. The transparent parts may be made of unbreakable glass or of appropriate transparent synthetic materials.

The invention is not restricted to the embodiment described. Many modifications and additions are possible, without departing from the spirit of the invention. For example, storage tank 7 for the flushing liquid may also be provided with an electric heater by means of which the sterile water in the said tank may be held at a constant temperature, e.g. 37° C. The said heater may also be used to sterilize the water by boiling.

It is also possible to connect the said storage tank to a sterile-water unit and to provide the storage tank with a means for keeping the level of the liquid constant, the latter means being in the form of a light barrier or a float controlling the supply of liquid. It is also possible to locate a filter for bacteria before the storage tank, through which the liquid to be sterilized is passed by means of a pump. It is also possible to store the flushing liquid, and to sterilize it, elsewhere, allowing only the flushing-liquid supply hose to run to the three-way valve through the stand, so that the flushing-liquid supply line, and the drain line for the used flushing liquid, still run between the three-way valve and the stand.

I claim:

1. A device for filling and evacuating hollow organs in human and animal bodies, comprising, a catheter probe,
   an elevated storage tank of adjustable elevation,
   a collector vessel for liquid,
   a three-way suction valve,
   a collector vessel for solid fragments in the form of a waisted vessel made of a transparent material, the upper part of the vessel comprising both an inlet aperture and an outlet aperture serving as an overflow,
   hose connections between the storage tank and the three-way valve and the catheter probe, and between the three-way valve and the collector vessel for solid fragments and between the collector vessel for solid fragments and the collector vessel for liquid,
   said storage tank being connected to a liquid level indicator in the form of a transparent sight glass referenced to the level of a patient on an operating table or bed,
   and a thermometer located within the sight glass for taking the temperature of the liquid therein.

2. A device, as defined in claim 1, in which the suction valve comprises a cone having T-shaped through-passages,
   the cone being spring-pressed into a valve housing comprising a matching internal conical surface,
   the housing being provided with a closed oil chamber at the large end of the cone,
   the spring being arranged in the oil chamber between the cone and a screwed cover sealing off the oil chamber from the outside,
   the cone being mounted self-lubricatingly in the housing by axial pressure applied to the small end of the cone,
   the cone being mounted to rotate 180° in the housing,
   the small end of the cone being connected to an actuating member.

3. A device, as defined in claim 1 or 2, in which the collector vessel is a waisted vessel of a transparent material,
   the upper part of the vessel having both an inlet aperture and an outlet aperture serving as an overflow,
   the lower part of the vessel having a removable opening for calculi and for fragments of calculi adapted to be closed off and sealed,
   the bottom of the calculus vessel being removable.

* * * * *